United States Patent [19]
Abbruscato

[11] Patent Number: 5,550,902
[45] Date of Patent: Aug. 27, 1996

[54] REMOTE STETHOSCOPE SIGNAL PROCESSING SYSTEM

[75] Inventor: C. Richard Abbruscato, Burnsville, Minn.

[73] Assignee: American TeleCare, Inc., Minneapolis, Minn.

[21] Appl. No.: 291,950

[22] Filed: Aug. 17, 1994

[51] Int. Cl.$^6$ ............................ H04M 11/00; A61B 7/04
[52] U.S. Cl. ........................... 379/106; 379/110; 381/67
[58] Field of Search ................................. 379/106, 107, 379/38, 90, 110; 381/67

[56] References Cited

U.S. PATENT DOCUMENTS

| | | |
|---|---|---|
| 3,426,150 | 2/1969 | Tygart . |
| 3,767,859 | 10/1973 | Doering et al. . |
| 3,810,102 | 5/1974 | Parks, III et al. . |
| 3,819,863 | 6/1974 | Slaght . |
| 3,863,625 | 2/1975 | Viglione et al. . |
| 3,872,252 | 3/1975 | Malchman et al. . |
| 3,882,277 | 5/1975 | DePedro et al. . |
| 3,886,314 | 5/1975 | Pori . |
| 4,055,729 | 10/1977 | Vandling . |
| 4,097,691 | 6/1978 | Ehrlich et al. . |
| 4,151,513 | 4/1979 | Menken et al. ..................... 379/106 |
| 4,173,971 | 11/1979 | Karz . |
| 4,220,160 | 9/1980 | Kimball et al. ..................... 381/67 |
| 4,281,664 | 8/1981 | Duggan . |
| 4,291,198 | 9/1981 | Anderson et al. . |
| 4,325,383 | 4/1982 | Lacks . |
| 4,337,377 | 6/1982 | Van Riper et al. . |
| 4,428,381 | 1/1984 | Hepp . |
| 4,593,284 | 6/1986 | Clifford et al. . |
| 4,594,731 | 6/1986 | Lewkowicz ......................... 381/67 |
| 4,598,417 | 7/1986 | Deno ................................... 381/67 |
| 4,723,555 | 2/1988 | Shue . |
| 4,731,849 | 3/1988 | Bloomfield, III ................... 381/67 |
| 4,754,762 | 7/1988 | Stuchl . |
| 4,883,064 | 11/1989 | Olson et al. . |
| 4,889,134 | 12/1989 | Greenwold et al. . |
| 4,920,558 | 4/1990 | Hird et al. . |
| 4,977,899 | 12/1990 | Digby et al. . |
| 5,226,086 | 7/1993 | Platt . |
| 5,226,431 | 7/1993 | Bible et al. . |
| 5,321,618 | 6/1994 | Gessman ............................. 379/38 |
| 5,333,171 | 7/1994 | Wang et al. . |
| 5,357,427 | 10/1994 | Langen et al. . |
| 5,367,555 | 11/1994 | Isoyama . |
| 5,418,686 | 5/1995 | Dieken et al. . |

FOREIGN PATENT DOCUMENTS

94/13206 6/1994 WIPO ..................................... 381/67

OTHER PUBLICATIONS

J. L. Crouch, "Electrocardiograms By Telephone", Bell Laboratories Record, pp. 43–47, Feb. 1966.

*Primary Examiner*—Wing F. Chan
*Attorney, Agent, or Firm*—Patterson & Keough, P.A.

[57] ABSTRACT

The present invention relates to a remote stethoscope system that allows a doctor at one location to listen to the stethoscope sounds coming from a stethoscope being used by a patient in his or her remotely-located home. The acoustic stethoscope sounds are converted into electrical signals, frequency shifted up to the telephone band, and then conveyed over a conventional telephone line. At the doctor's location, the signals are shifted down to their original frequencies and then converted back to audible sound for the doctor's analysis. The sensor used by the patient picks up a wide range of frequencies without any manipulation by the patient.

12 Claims, 5 Drawing Sheets

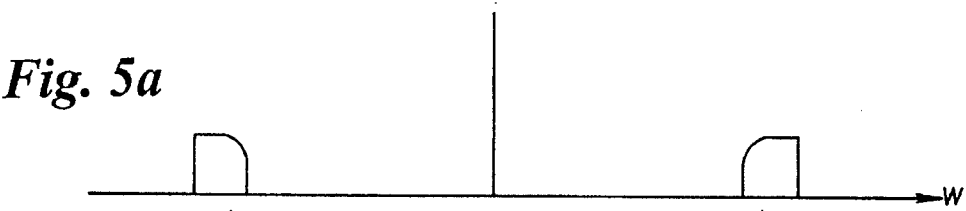
*Fig. 5a*
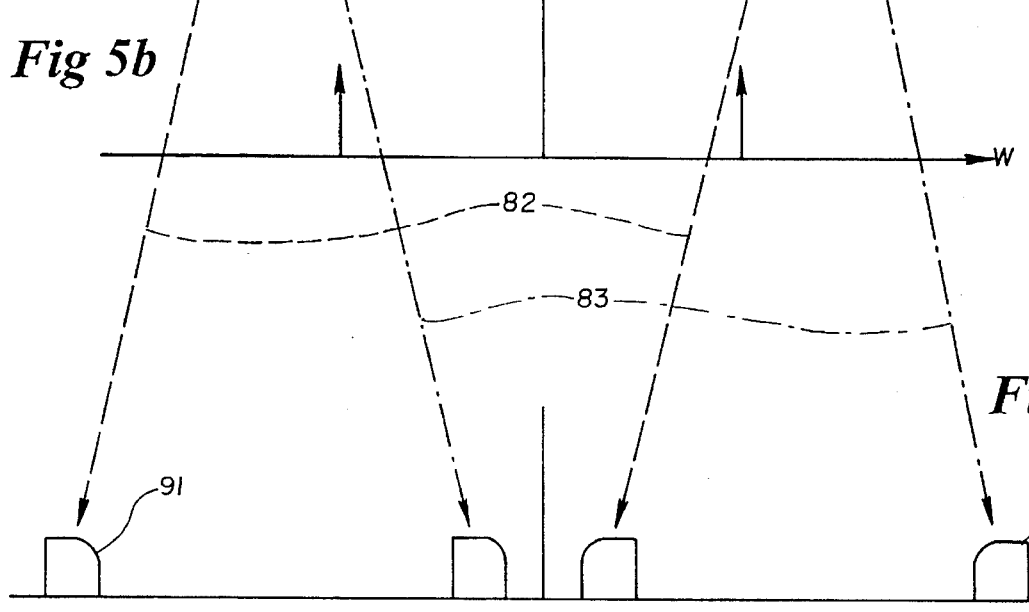
*Fig 5b*
*Fig. 5c*

REMOTE STETHOSCOPE SIGNAL PROCESSING SYSTEM

FIELD OF THE INVENTION

The present invention relates to stethoscope devices. More specifically, the present invention describes a system that enables a doctor or other health care provider to perform a stethoscope examination on a remotely-located patient.

BACKGROUND OF THE INVENTION

A stethoscope examination is a fundamental medical examination procedure that is part of any routine examination performed by a physician. A stethoscope examination allows the physician to analyze a patient's cardiovascular and respiratory system. To perform this analysis, the doctor uses an acoustic stethoscope to listen to the sounds generated by the patient's cardiovascular and respiratory system. The typical examination involves a doctor placing a stethoscope bell-and-diaphragm chest piece on a patient's back or chest so that the doctor is able to listen to sounds at various locations on the patient's body. The bell acts as a filter to isolate sounds in a lower frequency range, while the diaphragm filters out lower frequencies and passes higher frequency stethoscope sounds.

Although a stethoscope examination is a simple and routine procedure, it nevertheless requires that a patient be present with the doctor in an examination room. Consequently, those patients who may require frequent—perhaps even daily—stethoscope examinations are burdened by the administrative, financial, and logistical hardships involved in frequent visits to a doctor.

Patients who live a long distance from a doctor's office are particularly burdened. Patients residing in a remote location with a need to frequently see a doctor must either be admitted into a hospital (or other local facility), or be willing to hire a health care professional to visit or stay with the patient at the patient's home. For most patients, today's spiraling medical costs place both of these options out of reach.

There exists a compelling need, therefore, for a system by which a doctor can perform medical examinations on a remotely-located patient while avoiding at least some of the usual administrative, financial, and logistical hardships. Preferably, such a system would enable the doctor to perform a medical examination on a patient (such as a stethoscope examination) while the patient resides in the comfort of his or her home. Such a system would eliminate the need for the patient to travel to a doctor's office for routine stethoscope examinations. Such a system may, in some cases, also permit a patient who needs continual medical care to reside at home without hiring a health care provider to regularly visit the patient's home.

While many techniques for sensing and transmitting data from remote locations are known, acoustic stethoscope data sensed at a private home poses special problems. Fidelity of the signal presented to the doctor's ears is of utmost importance, because the doctor's diagnosis depends on subtle sound patterns. The sounds of greatest interest are relatively low frequencies (e.g., 30 to 500 Hz). But the most available data transmission channel—the ordinary home telephone line—transmits this range of frequencies very poorly.

Techniques for digitizing signals representing sounds are now well known, but the required sampling rates for good fidelity lead to bandwidth requirements that are not met by ordinary home telephone lines. And even if telephone lines could be upgraded (with attendant expense), the electronics required to digitize sound, compress the sound data, transmit the data by modem and perform the reverse at the receiving end is quite expensive. Moreover, because the loss of a single bit could result in significant distortion of the sound ultimately reconstructed, error detection/correction circuitry must be used, adding further to the costs.

Accordingly, any system used to facilitate remote stethoscopic or other medical examinations must be both cost-effective and accurate, if it is to be more efficient than a face-to-face consultation. In addition, it must provide sounds in the traditional manner, in accordance with physicians conventional stethoscope training.

SUMMARY OF THE INVENTION

The present invention relates to a remote stethoscope system that is used to allow a doctor or other health care provider at one location to listen to the stethoscope sounds coming from an acoustic transducer being used with a patient at a remote location. The acoustic sounds taken from the patient are converted into electrical signals. The electrical signals are then processed by analog techniques so that they can be transmitted over a conventional telephone network and accurately recovered at the doctor's location. At the doctor's location, the signals are converted back to audible sound for the doctor's analysis. The doctor can select one frequency range of particular interest.

It is an object of the present invention to provide a system that enables a doctor to perform a stethoscope examination on a remotely-located patient.

It is a further object of the present invention to enable a doctor to more easily and conveniently perform a stethoscope examination.

It is a still further object of the present invention to provide a system that permits a patient to conveniently undergo a stethoscope examination.

With these and other objects, advantages, and features of the invention that may become hereinafter apparent, the nature of the invention may be more clearly understood by reference to the following detailed description of the invention, the appended claims, and to the several drawings herein.

BRIEF DESCRIPTION OF THE DRAWINGS

FIGS. 5(a), 5(b), and 5(c) are spectral density graphs showing how the post-transmission signal (FIG. 5(a)) is mixed with a local oscillator (FIG. 5(b)) to recover the original signal.

DETAILED DESCRIPTION

Figure 1:
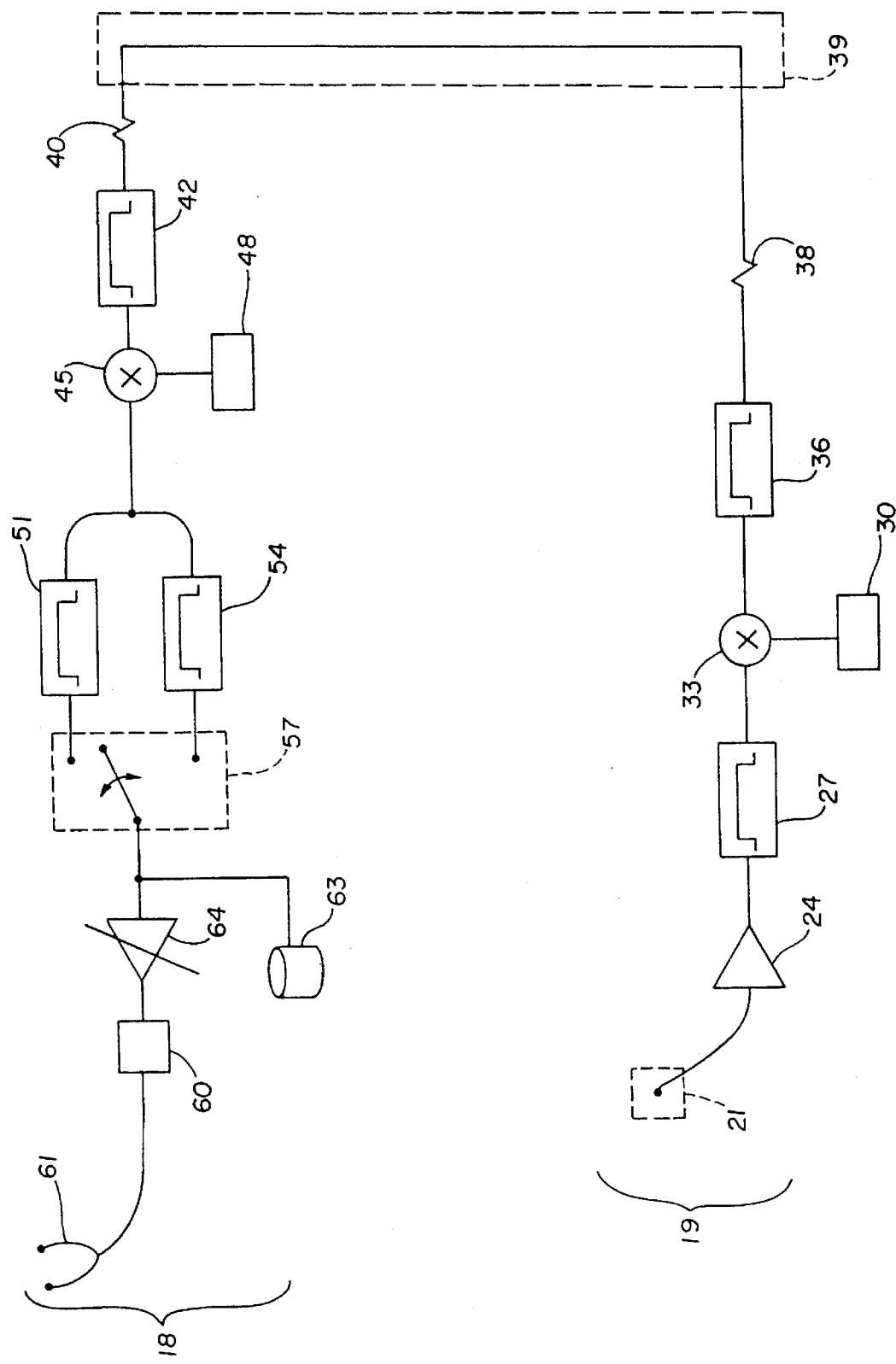
FIG. 1 is a block diagram of one embodiment of the present invention.

FIG. 1 shows a remote stethoscope system that permits a health care provider to examine a remotely-located patient. The remote stethoscope system can be thought of as having two parts: a remote stethoscope 19 and a local analyzer 18. The remote stethoscope 19 includes the equipment that is located at the remote location. The remote location is the patient's location, which is typically the patient's home. If any operation of the remote stethoscope 19 is required, it is typically done by the patient. Therefore, it is preferred that the remote stethoscope 19 be very easy to use.

Local analyzer 18 includes the equipment at the provider location. The provider location is the doctor's location, so the doctor (or nurse) operates the local analyzer equipment. Normal telephone lines are used to connect the remote stethoscope 19 and the local analyzer 18.

The remote stethoscope 19 comprises a number of elements. A stethoscope sensor 21 picks up acoustic signals from the patient and converts them into an electrical signal. A conventional acoustic stethoscope has a chest piece for picking up acoustic signals from the patient. The chest piece has a diaphragm on one side and a bell on the other. The bell is well suited for picking up low frequency acoustic signals, whereas the diaphragm is well suited for picking up higher frequency acoustic signals. The doctor uses the bell side of the chest piece when listening to the lower frequency sounds from the heart or blood vessels. To listen to higher frequency respiratory sounds, the doctor turns the chest piece over to use the diaphragm.

The precise range of frequencies picked up by stethoscopes can vary, and there is no standard or agreed-upon stethoscope frequency range. For example, some stethoscopes may pick up frequencies as high as 1400 Hz. See, e.g., The Illustrated Science and Invention Encyclopedia, p. 2255 (H. S. Stuttman 1983). In such a stethoscope, the bell might pick up frequencies ranging from 30 to 500 Hz, and the diaphragm might pick up frequencies ranging from 200 to 1400 Hz. Id. In other stethoscopes, however, a narrower range of frequencies will probably be more appropriate.

The sensor 21 in FIG. 1 is capable of picking up the acoustic sounds over a stethoscope frequency band that is sufficiently large to be useful to a doctor or health care provider. This stethoscope frequency band is herein defined as that range of frequencies that includes any band that the doctor may want to listen to through a stethoscope. The stethoscope frequency band must include the frequency band occupied by both (a) the low-frequency sounds generated by the patient's heart and blood vessels and (b) the higher-frequency sounds generated by the patient's respiratory system. The stethoscope frequency range can vary depending on the implementation, and it need not be contiguous. But in some embodiments, it may be important that the sensor 21 is capable of picking up acoustic signals from a patient ranging from 20 to 1400 Hz. But in other embodiments, it may not be necessary that the sensor 21 be capable of picking up such a wide range. In the preferred embodiment, for example, only the signals in the 20 to 500 Hz range are of interest, so the stethoscope frequency band is 20 to 500 Hz. Theoretically, in this preferred embodiment, one could get by with a sensor 21 that only picks up frequencies in the 20 to 500 Hz range (stethoscope frequency band).

The sensor 21 can therefore be a microphone with an acoustic coupler chest piece, capable of sensing sounds over a wide range of frequencies, and converting the sounds to electrical signals. But unlike the conventional chest piece, the sensor 21 does not have to be turned or manipulated so as to pick up or filter a given range of frequencies. The sensor 21 picks up the sounds in the full stethoscope frequency band without any manipulation by the patient.

Figure 2A:
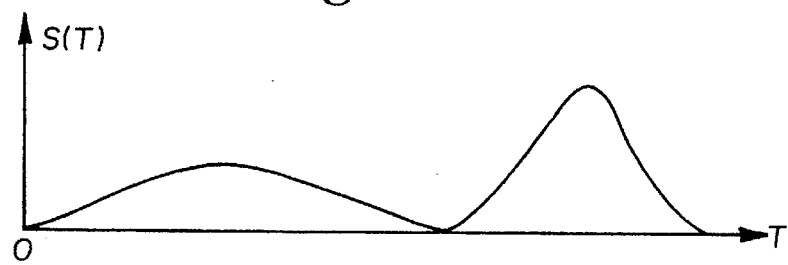
FIG. 2(a) is a simplified example of how a graph of amplitude versus time might look for an electrical signal generated by a stethoscope sensor.
Figure 2B:
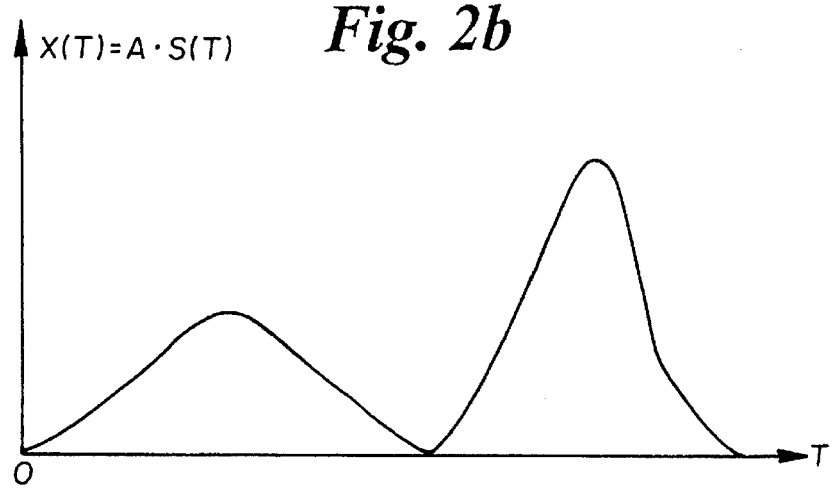
FIG. 2(b) is a graph of the signal of FIG. 2(a) after that signal has been amplified.

In FIG. 1, the original electrical signal from the sensor 21 is amplified by a amplifier 24. FIG. 2(a) shows a graph of what the original signal s(t) from the sensor 21 might look like. (FIG. 2(a) is merely meant to be a simple example of the infinite variety of signals that might be picked up by the sensor 21.) FIG. 2(b) shows the amplified signal x(t). A sensor filter 27 is used to suppress portions of the signal x(t) that are not within the stethoscope frequency band. The sensor filter 27 only reduces unwanted noise, so it may be omitted in some embodiments.

The original electrical signal generated by sensor 21 from the acoustic stethoscope sounds and amplified by the amplifier 24 is generally too low in frequency to pass undistorted over a normal telephone line. The stethoscope frequency band includes frequencies as low as 20 Hz. A pre-transmission mixer 33 is therefore used to shift the frequency of the original electrical signal from the sensor 21 up into a more distortion-free part of the telephone frequency band. The preferred telephone frequency band is a frequency range in which signals will pass over a telephone line with minimal distortion, which is typically 1000 Hz to 1500 Hz or so; but this range may vary, depending on the telephone network. By shifting lower frequency signals up into the preferred telephone frequency band, the signals will be able to pass over the telephone line with significantly less distortion.

Figure 3A:
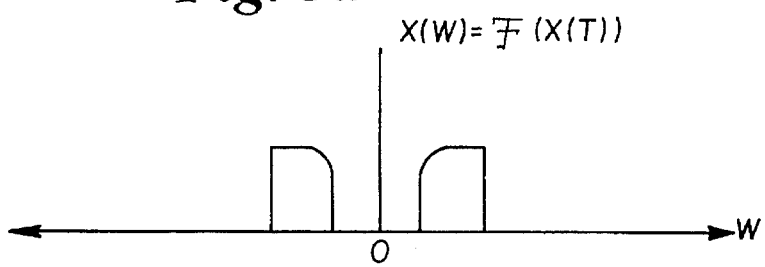
FIG. 3(a) is a graph of the Fourier transformation of the signal of FIG. 2(b).
Figure 3B:
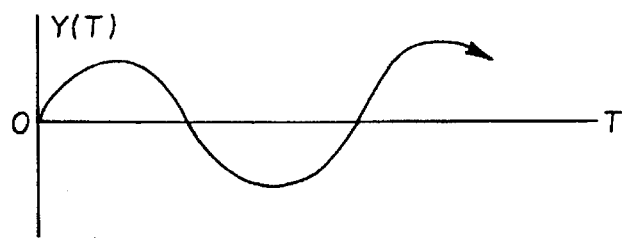
FIG. 3(b) is a graph of amplitude versus time for a local oscillator signal.
Figure 3C:
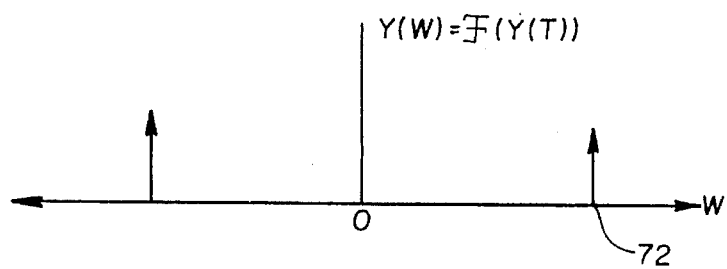
FIG. 3(c) is a graph of the Fourier transformation of the signal of FIG. 3(b).
Figure 3D:
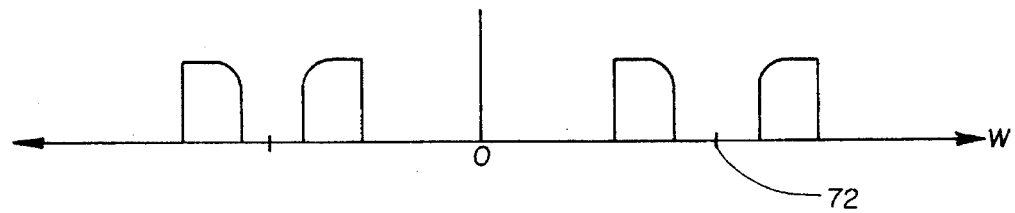
FIG. 3(d) is a graph of the Fourier transformation of the signal generated by mixing the signals of FIGS. 2(b) and 3(b).

To carry out the frequency-shifting function, the amplified signal x(t) is frequency-shifted using a pre-transmission mixer 33 and a local oscillator 30. The mixing operation is shown graphically in FIGS. 3(a) to 3(d). The Fourier transformation of x(t) is shown in FIG. 3(a) as X(w). A graph of a local oscillator signal y(t) is shown in FIG. 3(b) and the Fourier transformation of the signal y(t) is shown in FIG. 3(c) as Y(w). The pre-transmission mixer 33 shifts the signal x(t) from the sensor 21 and amplifier 24 up in frequency by an amount equal to a mixing frequency 72. The mixing frequency 72 is the frequency of the local oscillator 30. The mixing frequency can be any frequency that will shift the signal x(t) into the more distortion-free part of the telephone frequency band. The mixing frequency is somewhat dependent on the stethoscope frequency band because the mixing frequency must be chosen so that the signals in the stethoscope frequency band are shifted into the preferred telephone frequency band. For example, if the distortion-free part of the telephone frequency band (i.e., the preferred telephone frequency band) is 1000 Hz to 1500 Hz, then a 1000 Hz mixing frequency is appropriate if the stethoscope frequency band extends no higher than 500 Hz. A mixing frequency of 1000 Hz would also be appropriate if the stethoscope frequency band is smaller (e.g., 20 to 350 Hz). The spectral density of the mixed signal is the pre-transmission signal shown in FIG. 3(d). In the embodiment of FIG. 1, the output from mixer 33 is this pre-transmission signal.

Figure 4A:
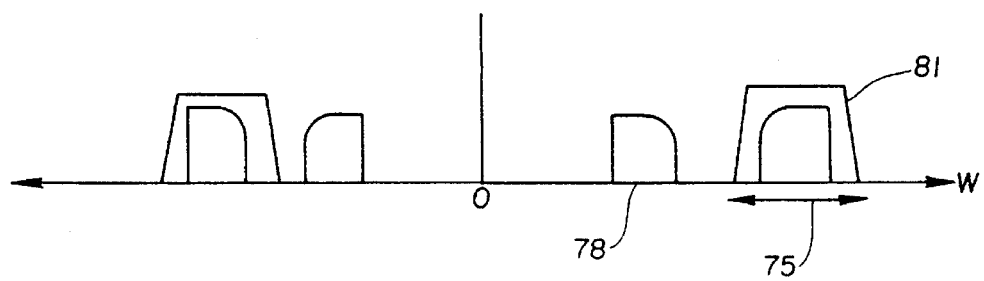
FIG. 4(a) is a spectral density graph illustrating how filters might be used in connection with the signal of FIG. 3(d).

The pre-transmission signal is then passed through a pre-transmission filter 36 (in FIG. 1) to suppress portions of that signal that are not within the preferred telephone frequency band 75 (as shown in FIG. 4(a)). The pre-transmission filter passband is shown graphically as 81 in FIG. 4(a). Specifically, the pre-transmission filter 36 suppresses the low-frequency image 78 generated by the pre-transmission mixer 33. The filtered signal (shown in FIG. 4(b)) is then sent over the telephone line via a standard interface 38 (approval per FCC part 68) to the telephone network 39.

Figure 4B:
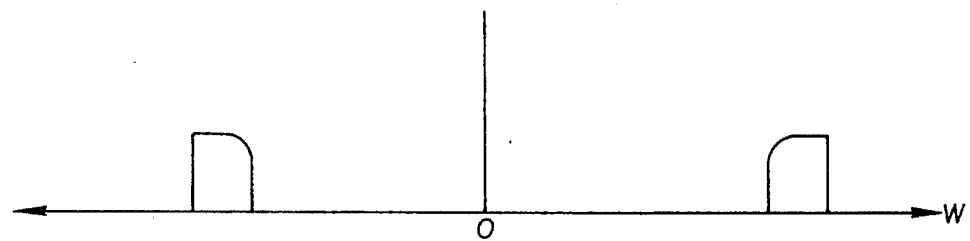
FIG. 4(b) is a spectral density graph showing the signal that results from the filtering of FIG. 4(b).

The local analyzer 18 receives the signal in FIG. 4(b) at the doctor's location through a reception interface 40 (approval per FCC part 68). A post-transmit filter 42 is used to suppress portions of the post-transmission signal that are not within the preferred telephone frequency band. The post-transmission signal received through the reception interface 40 is mixed at mixer 45 with the signal from a local oscillator 48. In this mixing step the post-transmission signal is shifted down in frequency by an amount equal to the mixing frequency 72 (which is the frequency of the local oscillator 48) so that the original electrical signal is recovered. The spectral density graphs of FIGS. 5(a) to 5(c) show the post-transmission signal (FIG. 5(a)), the local oscillator signal (FIG. 5(b)), and the recovered signal (FIG. 5(c)). The lines 82 and 83 illustrate how the graph of FIG. 5(a) is shifted in frequency.

The resulting signal in FIG. 5(c) provides a reproduction of the original stethoscope frequency band signal shown in FIG. 3(a), because the higher frequency images 91 and 92 can be easily removed by a low pass filter. After filtering, the signal shown in FIG. 5(c) is a suitably accurate reproduction of the original signal shown in FIG. 3(a).

The switch 57 at local analyzer 18 enables the doctor to select one of the two low-pass filters 51, 54 through which the signal is to be filtered. By manipulating the switch 57, the doctor isolates a particular frequency range (i.e., a desired frequency range) within the stethoscope frequency band that preferably will correspond to the bell or diaphragm mode of a conventional stethoscope. For example, in the embodiment shown in FIG. 1, a selection filter 51 filters all portions of the signal that are not within the higher stethoscope frequency band typically picked up by the diaphragm 23. These sounds correspond to the respiratory system, and an appropriate filter might pass only frequencies in the range of 100–500 Hz. Another selection filter 54 may filter all portions of the signal not within the lower stethoscope frequency band typically picked up by the bell 22, thereby isolating sounds that correspond to the cardiovascular system and blood vessels. An appropriate filter for this purpose might pass only frequencies in the range of 20–120 Hz. (The ranges described are merely for illustration in a non-limiting sense.)

Figure 6A:
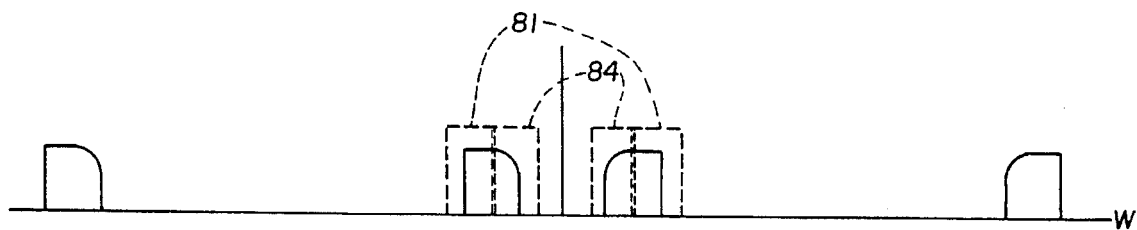
FIGS. 6(a), 6(b), and 6(c) are spectral density graphs illustrating how a selector can be used to isolate particular frequency ranges for analysis by a health care provider.
Figure 6B:
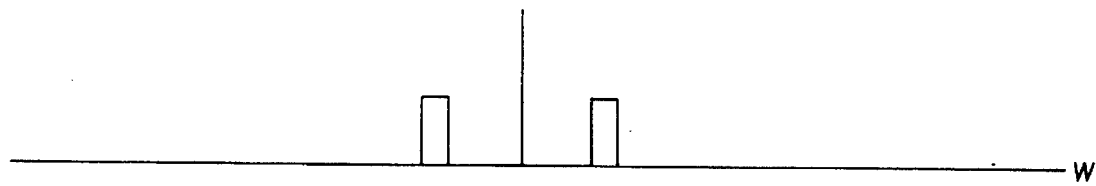
Figure 6C:
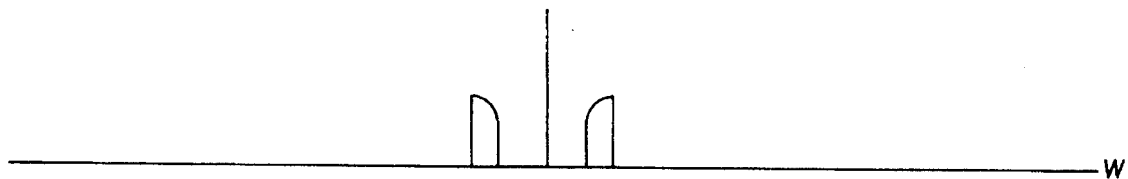

FIGS. 6(a) to 6(c) graphically illustrate this frequency range isolation, where the selection filter 51 is shown graphically in FIG. 6(a) as frequency range 81, and where selection filter 54 is shown graphically in FIG. 6(a) as frequency range 84. FIG. 6(b) shows the signal filtered by the higher stethoscope band filter 81. FIG. 6(c) shows the signal filtered by the lower stethoscope band filter 84. Therefore, if the doctor selects the higher selection filter 51, the resulting selected signal will correspond to the one shown in FIG. 6(b) (corresponding to selecting the stethoscope diaphragm). If the doctor selects the lower selection filter 54, the resulting selected signal will correspond to the one shown in FIG. 6(c) (corresponding to selecting the stethoscope bell).

In FIG. 6, the band of frequencies passed by selection filter 51 and selection filter 54 are immediately adjacent to each other. In other embodiments, however, the filters 51 and 54 can be designed so that the passbands of these filters may either overlap or have a gap of frequencies between them. If the passbands 81 and 84 of the filters overlap, for example, there will be a certain range of frequencies that will not be suppressed by either filter. If the passbands of the filters have a separating gap, a certain band of frequencies within the stethoscope frequency band will be suppressed by either filter.

In other embodiments, it is possible to have more than two filters from which a doctor can select, but the two filters 51 and 54 are shown so that the operation of present invention can be easily understood by those familiar with a conventional stethoscope. A larger number of selection filters might be appropriate if it is desirable to isolate more than the two traditional "bell" and "diaphragm" parts of the stethoscope frequency band. A larger number of selection filters might also be appropriate if a sensor were used that picks up a range of frequencies in addition to those in the conventional stethoscope frequency band. If more than two selection filters are used, the switch 57 would be adapted to allow a doctor to select one of the three or more selection filters.

After passing through one of the selection filters 51 or 54, a transducer 60 converts the selected, recovered signal from electrical form into acoustic signals. The doctor uses earpiece 61 to listen to the acoustic signals. FIG. 1 also shows a volume control 64 that can be controlled by the doctor to adjust the volume of the selected signal. A recording device 63 may also be employed as shown in FIG. 1 to store the sounds propagated through the system. The recording device enables the doctor to use, observe, or analyze the stored sounds at a later time.

In the embodiment shown in FIG. 1, the mixing operation is carried out before the selection filters isolate the desired frequency range. In an alternative embodiment, it is possible to perform the isolation step before shifting the signal back down to the original frequency range occupied by the signal prior to transmission. Another filter could be used in such an embodiment after the mixer to suppress any image signals generated by the mixer.

Although the present invention has been shown and described with respect to preferred embodiments, various changes and modifications that are obvious to a person skilled in the art to which the invention pertains, even if not shown or specifically described herein, are deemed to lie within the spirit and scope of the invention and the following claims.

What is claimed is:

1. A system for signal recovery in which a local oscillator frequency is selected to eliminate distortion of the signal and to yield a desired frequency band from a remote stethoscope system transmitting stethoscope sounds generated at a remote location over a telephone network to a provider location for evaluation by a health care provider, said telephone network having a characteristic telephone frequency band having a high end frequency, the system comprising:

a sensor for use with a patient, wherein said sensor is capable of picking up acoustic signals over a full stethoscope frequency band and converting said acoustic signals into an original electrical signal to provide a base band signal with a range of frequencies;

a first frequency shifting means for frequency shifting of said base band signal up to a preferred telephone frequency band, said first frequency shifting means including a local oscillator for generating a local oscillator frequency which is at least twice the highest frequency of said range of frequencies of said base band, said local oscillator frequency being no higher than said telephone frequency band high end frequency;

a first filtering means for filtering said shifted base band signal to suppress portions of said shifted base band signal that are not within said preferred telephone frequency band;

means for transmitting said shifted base band signal from said remote location over said telephone network to said provider location;

means for receiving said shifted base band signal from said telephone network at said provider location;

a second frequency shifting means for frequency shifting said shifted base band signal back down so that said original electrical signal is recovered;

a selection sensing means for sensing a selection made by said health care provider of a desired frequency band, wherein said desired frequency band spans only a portion of said full stethoscope frequency band;

a second filtering means for filtering said recovered original electrical signal to suppress portions of said recovered original electrical signal that are not within said desired frequency band; and means for converting said electrical signal to an acoustic signal.

2. A remote stethoscope system for a distortion free recovery of a predetermined frequency band wherein the predetermined frequency band is a portioned segment of the stethoscope frequency band, the system comprising:

a sensor for use with a patient, wherein said sensor is capable of picking up acoustic signals over a full stethoscope frequency band and converting said acoustic signals into an original electrical signal presenting a desired highest base band frequency;

a pre-transmission mixer, wherein said pre-transmission mixer converts said original electrical signal into a pre-transmission signal, wherein said pre-transmission signal is said original electrical signal shifted up in frequency by a mixing frequency to a preferred telephone frequency band, the mixing frequency being at least twice the value of said highest base band frequency;

a pre-transmission filter, operably connected to a said pre-transmission mixer, wherein said pre-transmission filter suppresses portions of said pre-transmission signal that are not within said preferred telephone frequency band;

a transmission interface, wherein said transmission interface transmits said pre-transmission signal through a telephone network, and wherein after passing through said telephone network, said pre-transmission signal is post-transmission signal;

a reception interface, wherein said reception interface receives said post-transmission signal;

a post-transmission mixer, wherein said post-transmission mixer converts said post-transmission signal into a recovered signal, wherein said recovered signal is said post-transmission signal shifted back down in frequency by said mixing frequency so that said original electrical signal is recovered;

a plurality of selection filters, wherein each of said selection filters is capable of receiving said recovered signal, and wherein each of said selection filters passes signals in only a portion of the stethoscope frequency band;

a selector, wherein said selector determines which of said plurality of selection filters is used to filter said recovered signal and thereby produce a selected signal; and a transducer, capable of receiving said selected signal, wherein said transducer converts said selected signal into a post-transmission acoustic signal.

3. The system of claim 2, said system further comprising:

an amplifier, operably connected to said sensor, wherein said amplifier amplifies said original electrical signal; and a sensor filter, operably connected to said amplifier and said pre-transmission mixer, wherein said sensor filter suppresses portions of said original electrical signal from said amplifier that are not within said stethoscope frequency band.

4. The system of claim 3, said system further comprising:

a post-transmission filter, operably connected to said reception interface, wherein said post-transmission filter suppresses portions of said post-transmission signal from said reception interface that are not within said preferred telephone frequency band.

5. The system of claim 4, said system further comprising:

a volume control, operably connected to said selector, wherein said volume control is capable of adjusting the volume of said selected signal.

6. The system of claim 2, said system further comprising:

an amplifier, operably connected to said sensor, wherein said amplifier amplifies said original electrical signal;

a sensor filter, operably connected to said amplifier and said pre-transmission mixer, wherein said sensor filter suppresses portions of said original electrical signal coming from said sensor that are not within said stethoscope frequency band;

a post-transmission filter, operably connected to said reception interface, wherein said post-transmission filter suppresses portions of said post-transmission signal from said reception interface that are not within said preferred telephone frequency band; and a volume control, operably connected to said selector, wherein said volume control is capable of adjusting the volume of said post-transmission acoustic signal.

7. A local analyzer for use with a remote stethoscope, wherein said local analyzer is operably connected to said remote stethoscope by a telephone network, wherein said remote stethoscope picks up acoustic signals over a full stethoscope frequency band and converts said acoustic signals into an original electrical signal of a predetermined portion of said full stethoscope frequency band for a distortion free recovery of the original signal, said local analyzer comprising:

a reception interface, wherein said reception interface receives a post-transmission signal;

a post-transmission mixer, wherein said post-transmission mixer converts said post-transmission signal into a recovered signal, wherein said recovered signal is said post-transmission signal shifted down in frequency by a mixing frequency so that said original electrical signal is recovered;

a plurality of selection filters, wherein each of said selection filters is capable of receiving said recovered signal, and wherein each of said selection filters passes signals in only a portion of said stethoscope frequency band;

a selector, wherein said selector determines which of said plurality of selection filters is used to filter said recovered signal and thereby produce the predetermined portion of said full stethoscope frequency band; and a transducer, capable of receiving the predetermined portion of said full stethoscope frequency band, wherein said transducer converts the predetermined portion of said stethoscope frequency band into a post-transmission acoustic signal.

8. The local analyzer of claim 7, said local analyzer further comprising:

a post-transmission filter, operably connected to said reception interface, wherein said post-transmission filter suppresses portions of said post-transmission signal from said reception interface that are not within a preferred telephone frequency band; and a volume control, operably connected to said selector, wherein said volume control is capable of adjusting the volume of said selected signal.

9. A local analyzer for use with a remote stethoscope, wherein said local analyzer is operably connected to said remote stethoscope by a telephone network, wherein said remote stethoscope picks up acoustic signals over at least a stethoscope frequency band and converts said acoustic signals into predetermined segments of an original electrical signal using a distortion free asynchronous recovery system, said local analyzer comprising:

a reception interface, wherein said reception interface receives said post-transmission signal;

a plurality of selection filters, wherein each of said selection filters is capable of receiving said post-transmission signal, and wherein each of said selection filters passes signals in only the predetermined segment of the original electrical signal comprising one of high frequency band and low frequency band of said stethoscope frequency band;

a selector, wherein said selector determines which of said plurality of selection filters is used to filter said post-transmission signal and thereby produce the predetermined segment of the original electrical signal;

a post-transmission mixer, wherein said post-transmission mixer converts the predetermined segment of the original electrical signal into a recovered signal, and wherein said recovered signal is the predetermined segment of the original electrical signal shifted down in frequency by a mixing frequency so that the predetermined segment of the original electrical signal is thereby recovered by the distortion free recovery system wherein said recovery system comprises, in combination, said selector, said post transmission mixer and a suppression filter; and said suppression filter including means for suppressing portions of said recovered signal that are not within said stethoscope frequency band.

10. A remote stethoscope for use with local analyzer, said remote stethoscope being operably connected to said local analyzer by a telephone network, said telephone network having a characteristic telephone frequency band having a high end frequency, said remote stethoscope comprising:

a sensor for use with a patient, wherein said sensor is capable of picking up acoustic signals over at least a stethoscope frequency band and converting said acoustic signals into an original electrical signal to form a base band having various frequencies;

a pre-transmission mixer, wherein said pre-transmission mixer mixes said base band with a mixer frequency that is at least twice the highest base band frequency, but is less than the telephone frequency band high end frequency to produce a pre-transmission signal;

a pre-transmission filter, operably connected to said pre-transmission mixer, wherein said pre-transmission filter suppresses portions of said pre-transmission signal that are not within said preferred telephone frequency band; and a transmission interface, wherein said transmission interface transmits said pre-transmission signal through said telephone network, and wherein after passing through said telephone network, said pre-transmission signal is post-transmission signal.

11. A method of transmitting stethoscope sounds generated at a remote location over a telephone network to a provider location for evaluation by a health care provider, said method comprising the steps of:

converting acoustic stethoscope signals at said remote location into a base band signal within a range of frequencies including a lowest and highest range;

frequency shifting said base band signal up to a preferred telephone frequency band;

filtering said shifted base band signal to suppress portions of said shifted base band signal that are not within said preferred telephone frequency band;

transmitting said shifted base band signal from said remote location over said telephone network to said provider location;

receiving said shifted base band signal from said telephone network at said provider location;

frequency shifting said shifted base band signal back down so that said base band signal is recovered;

sensing a selection made by said health care provider of a desired frequency band, wherein said desired frequency band spans only a portion of said stethoscope frequency band;

filtering said recovered base band signal to suppress portions of said base band signal that are not within said desired frequency band; and converting said recovered electrical signal to an acoustic signal.

12. The method of claim 11, said method further comprising the steps of:

filtering said base band signal to suppress portions of said base band signal that are not within said stethoscope frequency band, wherein said original base band signal is filtered after said converting acoustic stethoscope signals step but before said frequency shifting said original base band signal up step; and filtering said shifted base band signal to suppress portions of said base band signal that are not within said preferred telephone frequency band, wherein said shifted base band signal is filtered after said receiving said base band signal step but before said frequency shifting said base band signal back down step.

* * * * *